US010081810B2

(12) United States Patent
Ruan et al.

(10) Patent No.: US 10,081,810 B2
(45) Date of Patent: Sep. 25, 2018

(54) C-REL-SPECIFIC SIRNA AND ITS USE FOR PREVENTING AND TREATING AUTOIMMUNE PSORIASIS

(71) Applicants: Shenzhen Institutes of Advanced Technology, Shenzhen, Guangdong (CN); THE TRUSTEES OF THE UNIVERSITY OF PENNSYLVANIA, Philadelphia, PA (US)

(72) Inventors: Qingguo Ruan, Guangdong (CN); Youhai H. Chen, Philadelphia, PA (US); Tingting Fan, Guangdong (CN); Yifan Ma, Guangdong (CN); Lintao Cai, Guangdong (CN); Shaowen Wang, Guangdong (CN); Xiaochun Wan, Guangdong (CN)

(73) Assignees: SHENZHEN INSTITUTES OF ADVANCED TECHNOLOGY, Shenzhen, Guangdong (CN); THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 0 days.

(21) Appl. No.: 15/680,449

(22) Filed: Aug. 18, 2017

(65) Prior Publication Data
US 2018/0002698 A1    Jan. 4, 2018

Related U.S. Application Data

(63) Continuation of application No. PCT/CN2015/092124, filed on Oct. 16, 2015.

(51) Int. Cl.
*A61K 31/70* (2006.01)
*C07H 21/02* (2006.01)
*C07H 21/04* (2006.01)
*C12N 15/113* (2010.01)
*A61K 31/7105* (2006.01)
*A61K 9/00* (2006.01)
*A61K 9/107* (2006.01)
*C12N 5/00* (2006.01)

(52) U.S. Cl.
CPC ........ *C12N 15/1135* (2013.01); *A61K 9/0014* (2013.01); *A61K 9/1075* (2013.01); *A61K 31/7105* (2013.01); *C12N 2310/14* (2013.01); *C12N 2320/32* (2013.01)

(58) Field of Classification Search
None
See application file for complete search history.

(56) References Cited

U.S. PATENT DOCUMENTS

2010/0055116 A1    3/2010 Liou et al.

| | | | |
|---|---|---|---|
| 2011/0053861 A1* | 3/2011 | Xie | C12N 15/113 514/19.3 |
| 2015/0218109 A1* | 8/2015 | Liou | C07D 239/66 514/270 |

FOREIGN PATENT DOCUMENTS

| CN | 101460634 | 6/2009 |
|---|---|---|
| CN | 101646418 | 2/2010 |
| WO | 2007/100631 | 9/2007 |

OTHER PUBLICATIONS

Zheng et al., Biomaterials vol. 34(13):3431-3438, published online Jan. 31, 2013.*
International Search Report issued in the corresponding PCT application No. PCT/CN2015/092124, dated Aug. 3, 2016, 10 pages.
Zhao et al., "Role of IL-23/IL-17 Inflammatory axis in the pathogenesis of psoriasis-like lesions Induced by imiquimod in mice IL-23/IL-17", Chinese Journal of Pathophysiology, vol. 29, No. 6, Jun. 30, 2013, pp. 1086-1094.
Van der Fits et al., "Imiquimod-induced psoriasis-like skin inflammation in mice is mediated via the IL-23/IL-17 axis", Journal of immunology, vol. 182, No. 9, May 1, 2009, pp. 5836-5845, available at: http://www.jimmunol.org/content/182/9/5836.
Cai et al., "Dermal γδ (gamma and delta) T cells—A new player in the pathogenesis of psoriasis", International Immunopharmacology, vol. 16, 2013, pp. 388-391, abstract available at http://www.sciencedirect.com/science/article/pii/S156757691300060X?via%3Dihub.
Benham et al., "Th17 and Th22 cells in psoriatic arthritis and psoriasis", Arthritis Research & Therapy, vol. 15, 2013, 11 pages, available at: https://arthritis-research.biomedcentral.com/articles/10.1186/ar4317.
Campbell et al., "Distinct roles for the NF-kB1 (p50) and c-Rel transcription factors in inflammatory arthritis", The Journal of Clinical Investigation, vol. 105, No. 12, Jun. 2000, pp. 1799-1806.
Hilliard et al., "Critical roles of c-R, el in autoimmune inflammation and helper T cell differentiation", The Journal of Clinical Investigation, Sep. 2002, vol. 110, No. 6, pp. 843-850.
Lamhamedi-Cherradi et al., "Transcriptional Regulation of Type I Diabetes by NF-kB", The Journal of Immunology, vol. 171, 2003, pp. 4886-4892, available at: http://www.jimmunol.org/content/171/9/4886.
Ruan et al., "The Th17 immune response is controlled by the Rel-RORγ(gamma)-RORγ(gamma)T transcriptional axis", The Journal of Experimental Medicine, vol. 208, No. 11, 2011, pp. 2321-2333.
Carmody et al., "Essential Roles of c-Rel in TLR-Induced IL-23 p19 Gene expression in Dendritic Cells", The Journal of Immunology, vol. 178, 2007, pp. 186-191, available at: http://www.jimmunol.org/content/178/1/186.

(Continued)

Primary Examiner — Sean McGarry
(74) Attorney, Agent, or Firm — Hamre, Schumann, Mueller & Larson, P.C.

(57) ABSTRACT

The present invention provides a c-Rel-specific siRNA and its use for preventing and treating autoimmune psoriasis. In particular, the c-Rel-specific siRNAs have sequences as shown in SEQ ID Nos. 1-2 or SEQ ID Nos. 3-4. In the present invention, small interfering RNA (siRel) specific to c-Rel are employed to inhibit c-Rel biosynthesis, and prevent and treat autoimmune psoriasis by inhibiting inflammatory factors relating to IL-23/IL-17A inflammatory axis.

11 Claims, 5 Drawing Sheets

Specification includes a Sequence Listing.

(56) References Cited

OTHER PUBLICATIONS

Mason et al., "Cutting Edge: Identification of c-Rel-Dependent and -Independent Pathways of IL-12 production during infectious and inflammatory stimuli", The Journal of Immunology, vol. 168, 2002, pp. 2590-2594, available at: http://www.jimmunol.org/content/168/6/2590.

Tumang et al.,"IL-6 rescues the hyporesponsiveness of c-Rel deficient B cells independent of Bcl-xL, Mcl-1, and Bcl-2", Cellular Immunology, vol. 217, 2002, pp. 47-57.

Ruan et al., "Development of Foxp3+ Regulatory T Cells Is Driven by A c-Rel Enhanceosome", Immunity, vol. 31, No. 62, Dec. 18, 2009, pp. 932-940.

Vanderlugt et al., "Treatment of established relapsing experimental autoimmune encephalomyelitis with the proteasome inhibitor PS-519", The Journal of Autoimmunity, vol. 14, 2000, pp. 205-211.

May et al., "Selective inhibition of NF-κ(kappa)B Activation by a Peptide That Blocks the Interaction of NEMO with the Iκ(kappa)B Kinase Complex", Science, vol. 289, Sep. 1, 2000, pp. 1550-1554.

Deng et al., "Self-Assembled Cationic Micelles based on PEG-PLL-PLLeu Hybrid Polypeptides as Highly Effective Gene Vectors", Biomacromolecules, vol. 13, 2012, pp. 2795-3804.

Luo et al., "Cationic polypeptide micelle-based antigen delivery system: A simple and robust adjuvant to improve vaccine efficacy", Journal of Controlled Release, vol. 170, Sep. 10, 2013, pp. 259-267, abstract available at http://www.sciencedirect.com/science/article/pii/S0168365913003179?via%3Dihub.

Daniela De Stefano, "Oligonucleotides Decoy to NF-kappaB: Becoming a Reality", Discovery Medicine, vol. 12, Aug. 17, 2011, pp. 97-105, available at: http://www.discoverymedicine.com/Daniela-De-Stefano/2011/08/17/oligonucleotides-decoy-to-nf-kappab-becoming-a-reality/.

Oppmann et al., "Novel p19 Protein Engages IL-12p40 to Form a Cytokine, IL-23, with Biological Activities Similar as Well as Distinct from IL-12", Immunity, vol. 13, Nov. 2000, pp. 715-725, available at: http://www.cell.com/immunity/fulltext/S1074-7613(00)00070-4?_returnURL=http%3A%2F%2Flinkinghub.elsevier.com%2Fretrieve%2Fpii%2FS1074761300000704%3Fshowall%3Dtrue.

Lee et al., "Increased Expression of Interleukin 23 p19 and p40 in Lesional Skin of Patients with Psoriasis Vulgaris", The Journal of Experimental Medicine, vol. 199, No. 1, pp. 125-130, Jan. 5, 2004, available at: http://jem.rupress.org/content/199/1/125.

Langrish et al., "IL-23 drives a pathogenic T cell population that induces autoimmune inflammation", The Journal of Experimental Medicine, vol. 201, No. 2, pp. 233-240, Jan. 17, 2005, available at: http://jem.rupress.org/content/201/2/233.

Piskin et al., "In Vitro and In Situ Expression of IL-23 by Keratinocytes in Healthy Skin and Psoriasis Lesions: Enhanced Expression in Psoriatic Skin", The Journal of Immunology, vol. 176, pp. 1908-1915, 2006 available at: http://www.jimmunol.org/content/176/3/1908.

Harrington et al., "Interleukin 17—producing CD4+ effector T cells develop via a lineage distinct from the T helper type 1 and 2 lineages", Nature Immunology, vol. 6, No. 11, Nov. 2005, pp. 1123-1132, available at: https://www.nature.com/articles/ni1254.

* cited by examiner

C-REL-SPECIFIC SIRNA AND ITS USE FOR PREVENTING AND TREATING AUTOIMMUNE PSORIASIS

TECHNICAL FIELD

The present invention relates to treatment of autoimmune psoriasis by targeting c-Rel, a member of the NF-κB family, in particular to a c-Rel-specific siRNA and its use for the prevention and/or treatment of autoimmune psoriasis. The invention can effectively prevent and treat autoimmune psoriasis with almost no impact on the normal functioning of the immune system.

BACKGROUND

Psoriasis is one of the three most prevalent autoimmune diseases and has a global morbidity of about 3%, with one third of patients showing moderate to severe conditions. Psoriasis symptoms manifest in skin thickening, extensive lesions, could cause itching, scaling and pain, and have significant influence on the quality of life, mental health and social relationships of patients. In addition, patients having more severe conditions are more susceptible to complications such as arthritis, heart diseases and diabetes, and even risk of death.

1 Autoimmune Psoriasis 1.1 Advances in Pathogenesis Research on Autoimmune Psoriasis Until 1980, the researchers had paid only attention to the apparent psoriatic symptoms of psoriasis and believed that psoriasis was caused by excessive proliferation of skin keratinocytes. In the subsequent 20 years, with the development in immulogy, researchers detected in the skin of psoriasis patients significant increase of p40 protein, which was considered only a subunit of IL-12p35p40 at the time with IL-12p35p40 being an important factor driving the differentiation of naive CD4+ T cells into Th1 cells. Therefore, scholars at that time recognized psoriasis as an inflammatory disease mediated by abnormal activation of Th1 cells. However, in 2000, Oppmann B et al. discovered the p19 protein, which might polymerize with p40 to form IL-23p19p40. Thus, researchers realized that the theory of Th1-mediated psoriasis proposed on the basis of the difference in p40 expression was flawed. Consequently, Lee E et al. found upon further investigation that IL-23p19 and the p40 protein were both significantly increased in the skin of psoriasis patients but IL-12p35 was not significantly changed. In around 2005, Langrish C L, Harrington L E and Park H et al. found that IL-23 could promote the development of naive CD4+ T cells towards Th17 which regulated the inflammatory response mainly through the secretion of IL-17A. Currently, Leslie van der Fits et al. have demonstrated that autoimmune psoriasis was mediated primarily by the IL-23/IL-17A inflammatory axis (van der Fits, L. et al., Imiquimod-induced psoriasis-like skin inflammation in mice is mediated via the IL-23/IL-17 axis. *Journal of immunology* (*Baltimore, Md.*: 1950) 182, 5836-5845, doi:10.4049/jimmunol.0802999 (2009)). The pathogenetic process of this disease generally involves the following: pathogenic factors (e.g., genetics, environment, infection and physical lesions, etc.) induce the secretion of pro-inflammatory factors such as TNF-α, IL-1β, and IL-6 from innate immune cells (e.g., keratinocytes, natural killer cells), which then activates innate immune cells such as dendritic cells; the activated dendritic cells migrate to immune organs such as skin lymph nodes, present antigens and secret pro-inflammatory cytokines such as IL-23, promoting the differentiation of naive CD4+ T cells into Th17; the differentiated self-reactive Th17 migrates out of the skin capillaries, infiltrates the skin at the inflammatory sites; upon re-stimulation by autoantigens, it resumes proliferation and secrets many types of inflammatory cytokines such as IL-17A; the cytokines such as IL-17A can activate keratinocytes and stimulate their proliferation, leading to psoriasis symptoms; on the other hand, the activated keratinocytes can also secrete antimicrobial peptides (such as LL-37 antimicrobial peptide and β-defensin), pro-inflammatory cytokines (TNF-α, IL-1β and IL-6), chemokines (CXCL8-11, CCL20) and S100 proteins, which can in turn activate innate immune cells, leading to a vicious cycle of inflammation thereby maintaining and aggravating psoriasis. As such, IL-17A plays an important bridging role in the inflammatory circuit of innate and adaptive immune against psoriasis. Certainly, the IL-23/IL-17A inflammatory axis is only one important part of the pathologic processes of psoriasis. Recent studies have found that γδ T cells and macrophages could also secrete IL-17A and promote the pathogenesis of psoriasis (Cai, Y, Fleming, C. & Yan, J. Dermal gammadelta T cells—a new player in the pathogenesis of psoriasis. *International immunopharmacology* 16, 388-391, doi:10.1016/j.intimp.2013.02.018 (2013)), and Th22 cells could secrete IL-22 and aggravate the development of psoriasis, with the remaining pathological links yet to be found (Benham, H. et al. Th17 and Th22 cells in psoriatic arthritis and psoriasis. *Arthritis research & therapy* 15, R136, doi:10.1186/ar4317 (2013)).

1.2 Current Treatment Status for Autoimmune Psoriasis

At present, the treatment of psoriasis is classified mainly in accordance with the severity of the disease to be treated. Mild to moderate psoriasis is often treated with topical administration of drugs such as glucocorticoids, vitamin D3 analogues, vitamin A acid, anthralin, tar-based drugs, etc. For conditions in which the topical drugs are ineffective or for severe psoriasis, especially erythrodermic psoriasis, generalized pustular psoriasis and arthropathic psoriasis etc., a systemic dosing therapy is often used, such as intramuscular injection or intravenous infusion of small molecule immunosuppressive agents such as methotrexate and cyclosporine. In recent years, some biological formulations have also been approved by FDA for the treatment of severe psoriasis, such as monoclonal antibodies (mAbs) targeting T cell CD2 or CD11a, TNF-α, IL-12 and IL-23 (Table 1).

TABLE 1

Recent progress in research and development of psoriasis drugs

| Name | Pharma Company | Type | Target | R & D Progress |
|---|---|---|---|---|
| Alefacept | Biogen | mAb | T cell (CD2) | approved in 2003 |
| Efalizumab | Genentech | mAb | T cell (CD11a) | approved in 2003, and recalled in 2009 |
| Etanercept | Amgen | mAb | TNF-α | approved in 2004 |

TABLE 1-continued

Recent progress in research and development of psoriasis drugs

| Name | Pharma Company | Type | Target | R & D Progress |
|---|---|---|---|---|
| Infliximab | Janssen Biotech | mAb | TNF-α | approved in 2006 |
| Adalimumab | Abbott | mAb | TNF-α | approved in 2008 |
| Ustekinumab | Johnson, Janssen Biotechnology | mAb | p40 (IL-12&IL-23) | approved in 2009 |
| Briakinumab | Abbott | mAb | p40 (IL-12&IL-23) | Clinical phase 3 completed |
| Tildrakizumab | Merck | mAb | IL-23p19 | Clinical phase 3 |
| Guselkumab | Janssen Biotech | mAb | IL-23p19 | Clinical phase 3 |
| AMG-139 | Amgen | mAb | IL-23p19 | Clinical phase 2 |
| BI-655066 | Boehringer Ingelheim | mAb | IL-23p19 | Clinical phase 2 |
| LY-3074828 | Eli Lilly | mAb | IL-23p19 | Clinical phase 1 |
| ABT-122 | Abbott and Abb Vie | mAb | IL-17A & TNF | approved in 2009 |
| Secukinumab | Novartis | mAb | IL-17A | approved in 2015 |
| Brodalumab | Amgen | mAb | IL-17RA | Clinical phase 3 |
| Ixekizumab | Eli Lilly | mAb | IL-17A | Clinical phase 3 |
| Apremilast | Celgene | small molecule | PDE4 | approved in 2014 |
| AN2728 | Anacor | small molecule | PDE4 | Clinical phase 2 |
| Tofacitinib | Pfizer | small molecule | JAK | Clinical phase 3 |
| IM0-3100 | Idera | small molecule | TLR7 & 9 | Clinical phase 2 |

These biological formulations have significant efficacy but unknown safety, which need long-term clinical investigation. In addition, major pharmaceutical companies are also actively developing mAb drugs targeting IL-23, IL-17 or IL-17 receptors, among which is Secukinumab, the first IL-17 mAb in the world, developed by Novotis and approved by EU in early 2015. Unfortunately, for safety reasons, patients of mild to moderate degree cannot use these mAb drugs in a short term. In addition to the macromolecular monoclonal antibody drugs, some small molecule inhibitors have also been approved by FDA for the treatment of psoriasis, such as oral small molecule inhibitors targeting PDE4, and also small molecule inhibitors targeting TLR7 & 9 and JAK currently under clinical trials.

2 NF-κB family and its member c-Rel 2.1 NF-κB family and its members

The relationship between NF-κB family and its member c-Rel and autoimmune diseases has been reported in current fundamental researches. The NF-κB family of mammals is consisted of five members: c-Rel, RelA (p65), RelB, NF-κB1 (p50/p105), and NF-κB2 (p52/p100). The amino terminus of these proteins has a highly-conserved domain consisted of about 300 amino acid residues, referred to as the Rel homologous domain (RHD). This homologous domain functions in dimerization, interaction with IκB, nuclear localization, and binding to DNA. In contrast, the carboxyl terminus of these proteins is not conserved, and c-Rel, RelA and RelB have a transactivation domain at their carboxy terminus.

Newly synthesized NF-κBs are usually in homologous or heterologous dimeric forms that are bound to IκB and stored in the cytoplasm in an inactive state. Till now, nine members of the mammalian IκB family have been found: IκBα, IκBβ, IκBε, IκBζ, IκBη, BCL-3, IkB-NS, p100 (p52 precursor protein), and p105 (p50 precursor protein). These proteins prevent NF-κB from migrating into the nucleus mainly by covering the nuclear localization sequences of NF-κB family members. Some receptors, including receptors of tumor necrosis factor, IL-1 and nerve growth factor (NGF), T-cell and B-cell antigen receptors, and Toll-like receptors, can activate NF-κB upon binding to corresponding ligands. The activation of NF-κB requires IκB phosphorylation mediated by IκB kinases (IKK) and subsequent IκB protein degradation or processing (e.g., p100). Once NF-κB is activated, it enters the nucleus in a free dimeric form and binds to 9-10 base pairs in the promoter of the target gene to regulate the expression of the gene. The activated NF-κB can be down-regulated through a variety of mechanisms (such as feedback pathway), bound with newly synthesized IκB, and stored in the cytoplasm in a resting state.

2.2 C-Rel is Closely Related to the Development of Autoimmune Diseases

Studies have shown that NF-κB plays a critical role in the development of autoimmune diseases in addition to its role in maintaining physiological functions and pathological states. In mice and humans, the onset of type 1 diabetes is often accompanied by a high level activation of NF-κB in dendritic cells and mononuclear cells, as well as infiltration of these cells in tissues. Inhibiting activation of NF-κB can effectively inhibit the occurring of type 1 diabetes in NOD mice, CD1 mice and C57BL/6 mice (Campbell, I. K., Gerondakis, S., O'Donnell, K. & Wicks, I. P. Distinct roles for the NF-kappaB1 (p50) and c-Rel transcription factors in inflammatory arthritis. *The Journal of clinical investigation* 105, 1799-1806, doi:10.1172/jci8298 (2000)). To directly investigate the role of NF-κB in the development of autoimmune diseases, Liou et al. (together with the laboratory of the present inventors) used c-Rel and p50 knocked-out mice as experimental subjects to investigate the incidence of type I diabetes mellitus, arthritis and encephalomyelitis (B. A. Hilliard, N. Mason, L. Xu, J. Sun, S. E. Lamhamedi-Cherradi, H. C. Liou, C. Hunter, Y. H. Chen, Critical roles of c-Rel in autoimmune inflammation and helper T cell differentiation. The Journal of clinical investigation 110, 843-850 (2002); published online EpubSep (10.1172/jci15254); S. E. Lamhamedi-Cherradi, S. Zheng, B. A. Hilliard, L. Xu, J. Sun, S. Alsheadat, H. C. Liou, Y. H. Chen, Transcriptional regulation of type I diabetes by NF-kappa B. Journal of immunology (Baltimore, Md.: 1950) 171, 4886-4892 (2003); Q. Ruan, V. Kameswaran, Y. Zhang, S. Zheng, J. Sun, J. Wang, J. DeVirgiliis, H. C. Liou, A. A. Beg, Y. H. Chen, The Th17 immune response is controlled by the Rel-RORgamma-RORgamma T transcriptional axis. The Journal of experimental medicine 208, 2321-2333 (2011); published online EpubOct 24 (10.1084/jem.20110462)). These studies discovered that c-Rel knocked-out mice developed normally with an immune system of a normal constitution, not suffering from spontaneous infectious diseases, and when challenged with high-dose pathogens, they could clear pathogens with a normal or slight reduced clearing capacity. Meanwhile, C-Rel knocked-out mice were resistant to autoimmune diseases such as encephalomyelitis, type 1 diabetes, and arthritis. These phenomena suggest that c-Rel is closely related to the development of autoimmune diseases.

c-Rel and Inflammatory Response in Autoimmune Diseases

APC, T cells, and B cells in mice having autoimmune diseases are often associated with excessive activation of c-Rel, and the resistance of c-Rel knocked-out mice to the incidence of autoimmune diseases suggests that c-Rel plays a critical regulatory role in the pathogenesis of autoimmune diseases. Researches have shown that c-Rel was involved in regulating the expression of a number of inflammatory factors in antigen-presenting cells as well as the differentiation and development of Th17, mainly in the following aspects.

3.1 c-Rel Directly Regulates the Expression of a Number of Proinflammatory Factors in Antigen Presenting Cells Both dendritic cells and macrophages are specialized antigen presenting cells in the innate immune system of the body, which are capable of initiating the adaptive immune system. The inventors of the present invention found in a study on bone marrow-derived dendritic cells (BMDC) that the expression of IL-23p19 in c-Rel knocked-out BMDC was significantly lower than that in wild-type BMDC (Carmody, R. J., Ruan, Q., Liou, H. C. & Chen, Y. H. Essential roles of c-Rel in TLR-induced IL-23 p19 gene expression in dendritic cells. Journal of immunology (Baltimore, Md.: 1950) 178, 186-191 (2007)). It was found by in vitro luciferase assay (luciferase), gel migration assay (EMSA) and in vivo chromatin immunoprecipitation (ChIP) techniques that when Toll-like receptors (TLRs) conducted signal transduction, c-Rel could specifically bind to the IL-23p19 gene promoter at two binding sites and form a enhancer together with additional transcription factors to directly regulate IL-23p19 expression. Most importantly, when only the additional transcription factors (the p19 promoter also has potential binding sites for AP-1, C/EBP, and IRF) bound to the p19 gene promoter, the p19 gene was not activated, indicating that the expression of the IL-23p19 gene was completely dependent on c-Rel. Furthermore, Nicola Mason et al. found that during inflammatory stimulation (e.g., LPS), c-Rel in macrophages and dendritic cells directly regulated, in the form of a c-Rel/p50 heterodimer, the expression of IL-12p40 (N. Mason, J. Aliberti, J. C. Caamano, H. C. Liou, C. A. Hunter, Cutting edge: identification of c-Rel-dependent and -independent pathways of IL-12 production during infectious and inflammatory stimuli. Journal of immunology (Baltimore, Md.: 1950) 168, 2590-2594 (2002)). In addition, researches showed that c-Rel was also involved in regulating the expression of IL-6 and other pro-inflammatory factors in APC (J. R. Tumang, C. Y. Hsia, W. Tian, J. F. Bromberg, H. C. Liou, IL-6 rescues the hyporesponsiveness of c-Rel deficient B cells independent of Bcl-xL, Mcl-1, and Bcl-2. Cellular immunology 217, 47-57 (2002)).

3.2 c-Rel Directly or Indirectly Regulate the Differentiation and Development of Th17 Cells Previously, it was commonly recognized by researchers that Th1 cells were the primary pathogenic cells in the pathogenesis of autoimmune diseases. However, in recent years, it has been discovered in more in-depth studies that Th17 cells played a more critical pathogenic role in a variety of autoimmune diseases, including multiple sclerosis, psoriasis, rheumatoid arthritis and the like. Unlike Th1 cells, Th17 cells mainly produce cytokines such as IL-17A, IL-17F and IL-22, and play a role in inflammatory diseases and combating bacterial infections. Th17 lineage specific factors include RORγt, RORα and STAT3.

c-Rel affects the development and differentiation of Th17 in two aspects. In one aspect, as discovered by the present inventors, c-Rel indirectly regulates Th17 cell development by directly regulating IL-23 production in antigen presenting cells (Carmody, R. J., Ruan, Q., Liou, H. C. & Chen, Y. H. Essential roles of c-Rel in TLR-induced IL-23 p19 gene expression in dendritic cells. Journal of immunology (Baltimore, Md.: 1950) 178, 186-191 (2007)). In aother aspect, as found by the inventors, c-Rel can also directly regulate Th17 differentiation in T cells (Ruan, Q. et al. The Th17 immune response is controlled by the Rel-RORgamma-RORgamma T transcriptional axis. The Journal of experimental medicine 208, 2321-2333, doi:10.1084/jem.20110462 (2011)). When the inventors of the present application, Ruan, Q et al., used an anti-CD3 monoclonal antibody and an anti-CD28 monoclonal antibody to stimulate the CD4+ T cells isolated from c-Rel knocked-out mice, the expression of IL-17A messenger RNAs (mRNAs) and IL-17A proteins was significantly reduced in comparison with that in wild-type cells; and when the CD4+ T cells isolated from c-Rel knocked-out mice were cultured and stimulated in vitro, the number of Th17 was found to be reduced up to 70% (Ruan, Q. et al. The Th17 immune response is controlled by the Rel-RORgamma-RORgamma T transcriptional axis. The Journal of experimental medicine 208, 2321-2333, doi:10.1084/jem.20110462 (2011); Ruan, Q. et al. Development of Foxp3(+) regulatory t cells is driven by the c-Rel enhanceosome. Immunity 31, 932-940, doi:10.1016/j.immuni.2009.10.006 (2009)). Further studies showed that the expression of RORγ and RORγT was significantly decreased in c-Rel knocked-out T cells, while the reestablishment of RORγ and RORγT could restore the differentiation defects of Th17 in c-Rel knocked-out T cells. In addition, with the chromatin immunoprecipitation technique, Ruan, Q et al. found that c-Rel/p65 regulated the expression of RORγT and RORγ mRNAs by respectively binding and activating two different Rorγ promoters. Based on the results of the above studies, the inventors of the present application, Ruan, Q et al., proposed a Th17 differentiation theory: on the CD4+ T cells, when TCR, costimulatory molecules, and cytokine receptors such as IL-1, IL-23, and IL-6 binding with the corresponding ligands (Th17 differentiation conditions), activation signals are transducted into the cell, and multiple transcription factors were released into the nucleus. In this process, the free c-Rel/p65 dimer binds to different promoters of the Rorγ gene and interacts with other transcription factors (such as NFAT and Stat) that are released into the nucleus to form Rorγ-specific enhancers, initiating the transcription of the Rorγ gene, which drives the Th17 cells to differentiate. It is noteworthy that the c-Rel/p65 transcription factors are the only transcription factors currently found to bind to the Rorγ gene promoters and activate transcription, and other transcription factors binding to the Rorγ gene promoters remain to be discovered.

4 Treatment of Autoimmune Psoriasis by Targeting the Entire NF-κB Family

Theoretically, drugs targeting the entire NF-κB family may be effective in treating autoimmune psoriasis, such as protease inhibitors (e.g., the FDA-approved PS-341), NF-κB decoy oligonucleotides, NBD polypeptides, glucocorticoids and the like (Vanderlugt, C. L., Rahbe, S. M., Elliott, P. J., Dal Canto, M. C. & Miller, S. D. Treatment of established relapsing experimental autoimmune encephalomyelitis with the proteasome inhibitor PS-519. *Journal of autoimmunity* 14, 205-211, doi:10.1006/jaut.2000.0370 (2000); May, M. J. et al. Selective inhibition of NF-kappaB activation by a peptide that blocks the interaction of NEMO with the IkappaB kinase complex. Science 289, 1550-1554 (2000); De Stefano, D. Oligonucleotides decoy to NF-kappaB: becoming a reality? *Discovery medicine* 12, 97-105 (2011)). However, most of the NF-κB family proteins are commonly expressed in many cells in the body and are associated with the maintenance of normal physiological functions such as congenital and adaptive immunity regulation during infection, inflammatory response, anti-apoptosis, cell proliferation and the like. As a result, these drugs have severe side effects, poor specificity, and can only be used in a short term to control acute allergic reactions. Thus, those drugs that target the entire NF-κB family can not be used to treat chronic inflammatory diseases, such as autoimmune psoriasis.

SUMMARY OF INVENTION

One of the objects of the present invention is to inhibit c-Rel biosynthesis by employing a c-Rel-specific small interfering RNA (siRNA), so as to prevent and treat autoimmune psoriasis by inhibiting the IL-23/IL-17A inflammatory axis in mice with psoriasis.

Another object of the present invention is to provide a c-Rel-specific small interfering RNA which inhibits c-Rel biosynthesis in a subject. The subject can be a mammal (e.g., mice) or human.

Another object of the present invention is to provide a method for preventing and treating autoimmune psoriasis by delivering a c-Rel-specific small interfering RNA using nano-materials.

In the present invention, the c-Rel-specific small interfering RNA is referred to as siRel.

On account of the important role of c-Rel in inflammatory response and the pathogenesis of autoimmune psoriasis, the present invention proposes to target only the NF-κB family member c-Rel, and use a c-Rel-specific small interfering ribonucleic acid (siRel) to inhibit the biosynthesis of c-Rel, thereby preventing and/or treating autoimmune psoriasis by interfering with the IL-23/IL-17A inflammatory axis in a subject with psoriasis.

In one aspect, the present invention utilizes a c-Rel-specific small interfering RNA (siRel) to inhibit the biosynthesis of the NF-κB family member c-Rel, thereby preventing and/or treating autoimmune psoriasis by interfering with the IL-23/IL-17A inflammatory axis.

According to a specific embodiment of the present invention, the present invention provides a c-Rel-specific small interfering RNA (siRel). The c-Rel-specific small interfering RNA (siRel) can be used to inhibit c-Rel biosynthesis. In particular, the c-Rel-specific small interfering RNAs (siRels) in mice have sequences as below:

```
                                            (SEQ ID No. 1)
sense strand       5' CAACCGGACAUACCCGUCUdTdT 3'

(SEQ ID No. 2)
antisense strand   5' AGACGGGUAUGUCCGGUUGdTdT 3'
```

Correspondingly, the c-Rel-specific small interfering RNAs (siRels) in human have sequences as below:

```
                                            (SEQ ID No. 3)
sense strand       5' CAACCGAACAUACCCUUCUdTdT 3'

(SEQ ID No. 4)
antisense strand   5' AGAAGGGUAUGUUCGGUUGdTdT 3'
```

In another aspect, the present invention also provides a method for preventing and/or treating autoimmune psoriasis by delivering c-Rel-specific small interfering RNA (siRel) in nano-materials. In particular, a nano-micelle (e.g., a PEG-PLL-PLLeu tri-block copolymer nano-micelle) is used as a carrier to deliver the siRel to dendritic cells in vivo, for prophylactic and/or therapeutic purposes.

In another aspect, the present invention also provides use of a c-Rel-specific small interfering RNA in the preparation of a pharmaceutical composition for inhibiting the IL-23/IL-17A inflammatory axis in the subject with psoriasis by inhibiting the biosynthesis of c-Rel. In particular, the c-Rel-specific small interfering RNA has the sequence shown in SEQ ID Nos. 1 to 2 or SEQ ID Nos. 3 to 4. The pharmaceutical compositions may also include nano-materials (e.g., PEG-PLL-PLLeu tri-block copolymer micelles) for carrying the c-Rel-specific small interfering RNAs and transporting them into the cytoplasm.

In another aspect, the present invention also provides a pharmaceutical composition that comprises an effective amount of the c-Rel-specific small interfering RNA for preventing and/or treating autoimmune psoriasis. Preferably, the pharmaceutical composition further comprises a PEG-PLL-PLLeu tri-block copolymer nano-micelle. In addition, the pharmaceutical composition may include one or more pharmaceutically acceptable excipients. In a specific embodiment of the present invention, the pharmaceutical composition of the present invention may be a topical formulation (which may be in the form of a nano-micellar suspension for application on skin) for preventing and/or treating autoimmune psoriasis in a subject, wherein the c-Rel-specific small interfering RNA has a concentration of 10-100 nM, and the nano-micelle has a concentration of 10-20 μg/ml. The subject may be a mammal (e.g., mice) or human.

The present invention also provides a method of preventing and/or treating autoimmune psoriasis, comprising administering to a subject an effective amount of c-Rel-specific small interfering RNA to inhibit c-Rel synthesis and thus inhibit IL-23/IL-17A inflammatory axis in a subject with psoriasis. According to a particular embodiment of the present invention, the present invention provides a method of preventing and/or treating autoimmune psoriasis by using a nano-micelle to transport c-Rel-specific siRNA. Because of the disadvantages of siRNA drugs including low transfection efficiency, susceptibility to enzymatic hydrolysis in vivo, and short half-life, the present invention utilizes a PEG-PLL-PLLeu tri-block copolymer micelle to carry the siRNA and transport it into the cytoplasm. Researches of the present inventors show that this tri-block copolymer micelle is biodegradable, and has high transfection efficiency (Deng, J. et al. Self-assembled cationic micelles based on PEG- PLL-PLLeu hybrid polypeptides as highly effective gene vectors. *Biomacromolecules* 13, 3795-3804, doi:10.1021/bm3012538 (2012)). Most importantly, the researches of the present inventors show that such PEG-PLL-PLLeu tri-block copolymer micelle is predominantly enriched in spleen where it is taken up by dendritic cells (Luo, Z. et al. Cationic polypeptide micelle-based antigen delivery system: A simple and robust adjuvant to improve vaccine efficacy. *Journal of Controlled Release* 170, 259-267, doi:http://dx.doi.org/10.1016/j.jconrel.2013.05.027 (2013). For in vitro experiments, the siRel is used at a concentration of 10-100 nM, and the nano-micelle used at a concentration of 10-20 µg/ml. For in vivo experiments in mice, for the treatment of mild psoriasis, each mouse is administered intraperitoneally 500 pmol siRel, corresponding to 100 µg nano-micelle, given at a frequency of once every two days; for the treatment of moderate psoriasis, each mouse is administered intraperitoneally 500 pmol siRel, corresponding to 100 µg nano-micelle, given at a frequency of once every one day. In human body, intravenous administration, or intradermal, subcutaneous or on-skin application within skin lesions areas are employed. Specifically, the dosage of the siRel administered intravenously is 0.3 mg/kg, and the corresponding dosage of the nano-micelle is 4.5 mg/kg, given at a frequency of once every three weeks; the dosage of the siRel administered intradermally is 8 mg, and the corresponding dosage of the nano-micelle is 8 mg, given at a volume of 2 ml and at a frequency of once every one week; the dosage of the siRel administered subcutaneously is 16 mg, and the corresponding dosage of the nano-micelle is 16 mg, given at a volume of 4 ml and at a frequency of once every one week; or the siRel is applied on the skin at a concentration of 10 nM, and the corresponding dosage of the nano-micelle is 10 µg/ml, given at a frequency of 1 to 3 times every one day, with 0.5 ml of the siRel nano-micelle suspension applied per 500 square centimeters for each application.

According to a specific embodiment of the present invention, in a specific in vitro experiment of the present invention, the effectiveness of the c-Rel-specific siRNA (i.e., the siRel) of the present invention was confirmed in NIH3T3, BMDC and RAW264.7 cell lines. The present invention demonstrates that the siRels significantly reduce the mRNA and protein expression levels of c-Rel and IL-23p19.

According to a specific embodiment of the present invention, in a specific in vivo experiment of the present invention, it was found that the siRels could remarkably control the development of psoriasis in mice with mild psoriasis, significantly reduce the production of IL-17A in spleen cells of the mice, and inhibit the expression of IL-1β, IL-6, TNF-α, IL-23p19, and IL-17A in the skin lesion tissues of the mice, thereby achieving a therapeutic effect. In addition, the H & E staining results of skin dissections from two groups of mice show that the skin of the mice from the treated group was thinner than that of the control group, and the infiltrated inflammatory cells within the skin of the mice from the treated group was significantly reduced. In addition, evaluation of the siRel drug on mice with moderate psoriasis also shows certain therapeutic effect of such siRel drug.

In view of the above, in the present invention, by using a nano-micelle, c-Rel-specific siRNA can be efficiently transported into dendritic cells, significantly reducing the expression of inflammatory factors related to the IL-23/IL-17 inflammatory axis, effective in preventing and/or treating autoimmune psoriasis.

DETAILED DESCRIPTION OF THE INVENTION

For a clearer understanding of the essence of the invention, the invention will now be described in more details by way of specific examples with reference to the accompanying drawings, but the invention is not limited thereto in any way. In the following examples, the experimental processes for which the detailed conditions are not specified are generally carried out in accordance with routine practice in the field or in accordance with the conditions recommended by the manufacturer.

Example 1

In this example, the efficacy of the c-Rel-specific siRNA (i.e., siRel) was verified in NIH3T3 and RAW264.7 cell lines (the NIH3T3 and RAW264.7 cell lines were purchased from ATCC) in in vitro experiments. Furthermore, bone marrow-derived dendritic cells (BMDC) were used as investigating objects to verify the silencing effect of the siRel. The details of the experiments were as follows:

1. Design and Synthesis of c-Rel-Specific Small Interfering RNA (siRNA)

In this example, c-Rel-specific small interfering RNAs (siRel) were used to inhibit c-Rel synthesis, where the RNAs in mice have the sequences of

```
                                           (SEQ ID No. 1)
    sense strand      5' CAACCGGACAUACCCGUCUdTdT 3'

(SEQ ID No. 2)
    antisense strand  5' AGACGGGUAUGUCCGGUUGdTdT 3'
```

These siRel sequences were synthesized by Shanghai JiMa Inc. and siNC was used as a general negative control. FAM-labeled siRels (siRel-FAM) were also synthesized by Shanghai JiMa Inc.

2. Preparation of siRNA/PEG-PLL-PLLeu Micelle Suspension

PEG-PLL-PLLeu is a polyethylene glycol-polylysine-poly-leucine tri-block copolymer, synthesized by coworkers, MA Yifan and CAI Lintao, using NCA ring-opening polymerization (Deng, J. et al. Self-assembled cationic micelles based on PEG-PLL-PLLeu hybrid polypeptides as highly effective gene vectors. *Biomacromolecules* 13, 3795-3804, doi:10.1021/bm3012538 (2012)). In an aqueous solution, at a concentration greater than the critical micelle concentration, the amphiphilic tri-block copolymer could self-assemble to form micelles with a particle size of about 150 nm. In this case, poly-leucine segments aggregated to form the hydrophobic core of the micelle, polyethylene glycol formed the shell of the micelle, and the poly-lysine segments in the middle were protonated because they had a large amount of primary amino groups, resulting in a zeta potential of the micelle of about 43 mV. By electrostatic interaction, the nano-micelle could bind to the negatively-charged siRNA to form a positively-charged mixed suspension of siRNA-carrying micelles. In addition, because cell membrane was negatively charged, the siRNA-carrying nano-micelles were adsorbed on the cell membrane by electrostatic interaction, facilitating the endocytosis of the micelles by the cell.

Figure 1:
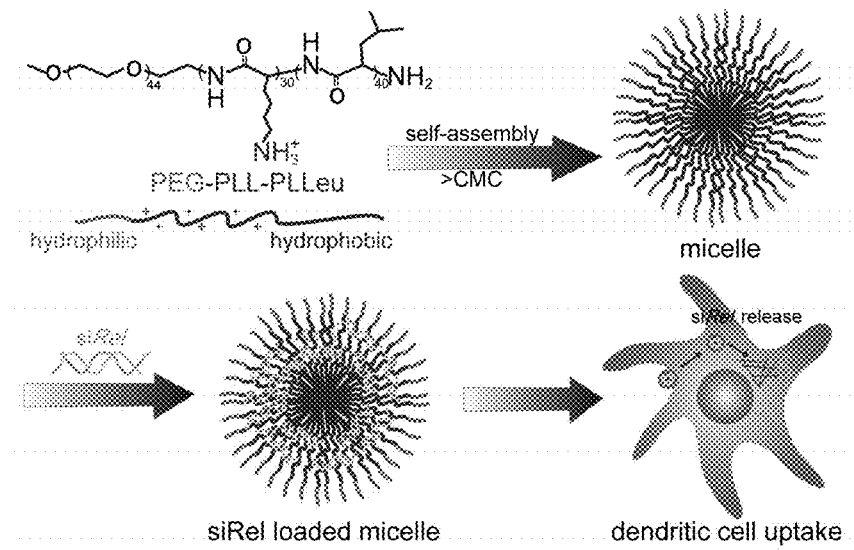
FIG. 1 illustrates an schematic illustration of preparation of the siRNA/PEG-PLL-PLLeu micelle suspension.

Referring to FIG. 1, an appropriate amount of PEG-PLL-PLLeu lyophilized powder was weighed and dissolved in deionized water, and 1 mg/ml copolymer micelle suspension was prepared and then subjected to sterilization through a 0.22 μm filter. The OPTI-MEM diluted siRel was mixed with an equivalent volume of the copolymer suspension at different N/P ratios (a molar ratio of the primary amino groups in the copolymer micelle to the phosphate groups in siRel), and left still at room temperature for 30 min, to obtain a siRel-carrying copolymer micelle (siRel/PEG-PLL-PLLeu) suspension. The micelle suspension was dropped into a cell culture plate and mixed uniformly under gentle tapping, for cell transfection.

3. Characterization of the siRNA/PEG-PLL-PLLeu Nano-Micelle

The siRel/PEG-PLL-PLLeu mixed at different N/P ratios prepared as described above were loaded on a 2% agarose gel, electrophoresed at 120 mV for 20 minutes by using a TAE buffer, and observed with a UV gel imaging device for gel retardation results. The particle size and zeta potential of the nano-micelles were measured at room temperature using a dynamic light scattering meter (Nano-ZSZEN3600) and analyzed with the Malvem Dispersion Technology Software 4.2 software.

Figure 2:
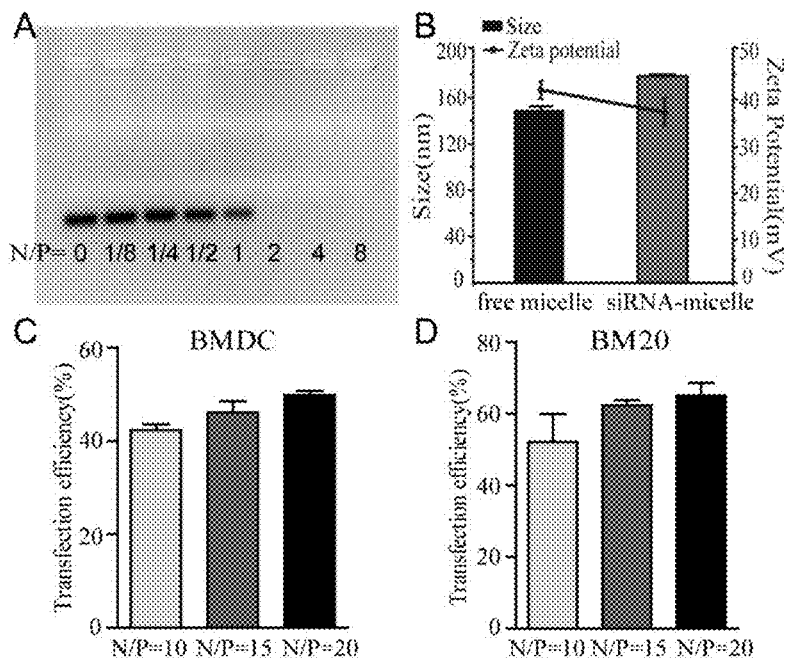
FIG. 2 illustrates a characterization of the siRNA/PEG-PLL-PLLeu nano-micelle, in which panel A shows a gel retardation assay for determining the capacity of the micelle in binding the siRNA; panel B shows the particle size and surface potential of the siRNA-carrying micellar mixture (N/P=15); and panels C and D show the determination of the efficiency of transfecting BMDC or BM20 by siRNA-carrying micellar mixtures having different N/P ratios. The values are shown as mean±standard deviation (n=3).

FIG. 2 shows in A the siRNA-binding ability of the micelles determined by the gel retardation assay. As seen from the figure, when the N/P ratio is greater than or equal to 2, the copolymer micelle can carry all the siRNA.

FIG. 2 shows in B the particle size and surface potential of the siRNA-carrying micelle mixtures (N/P=15). The results show that the micelles particle size increases from about 148 nm to about 180 nm, and the zeta potential decreases from about 42 mV to about 38 mV, when the micelles and siRNA are mixed at a N/P ratio of 15.

FIG. 2 shows in C and D the determined results of the efficiency of transfecting BMDC or BM20 with siRNA-carrying micelle mixtures mixed at different N/P ratios. Flow cytometry results show that there is no significant difference between the transfection efficiency for BMDC and that for BM20 when the N/P ratio is 10, 15, or 20. When the N/P ratio is 15, the BMDC is transfected with the nano-micelle at an efficiency of about 45%, while BM20 is transfected at an efficiency of about 60%.

4. In Vitro Silencing Experiment with siRel/PEG-PLL-PLLeu Nano-Micelle

METHOD: NIH3T3 and RAW264.7 cell lines were purchased from ATCC and cultured according to standard procedures. BMDC is obtained by primary isolation and induction. BALB/c mice were sacrificed by cervical dislocation, and femur and tibia were removed under sterile conditions. Bone marrow cells were rinsed out by pipetting PBS containing 2% FBS with a 1 ml syringe. The cell suspension was collected and resuspended with the erythrocyte lysate after centrifugation. The cells were washed three times with the culture medium 1 min after the lysis. Cells were suspended in the X-Vivo medium containing 20 ng/ml recombinant mouse GM-CSF and 10 ng/ml recombinant mouse IL-4, to prepare a cell suspension of $2\times10^6$ cells/ml, which was then seeded into a 24-well plate, with 1 ml per well. Half-volume exchange of the culture medium was carried out on day 3 and day 5, and bone marrow-derived dendritic cells (BMDC) were obtained on day 6. In assessing the in vitro silencing effect of the siRel, NIH3T3, RAW264.7 or BMDC was seeded in 24-well plates into which the prepared siNC-carrying or siRel-carrying nano-micelles were added dropwise, until the siRNA concentration in the culture medium was 100 nM. 24 h after transfection, the cells was stimulated with LPS or not stimulated for 6 h and then collected, and the total RNA was extracted from the cells or tissues using the Trizol reagent. Reverse transcription was performed using oligo dT as a primer and the M-MLV Reverse Transcriptase, while the specific experimental procedures were performed according to the instructions of the Promega product. The expression level of c-Rel and IL-23p19 mRNA was then determined by real-time quantitative PCR using Thunderbird SYBR qPCR Mix with GAPDH as an internal reference. After 48 hours of transfection, BMDC was stimulated with LPS for 6 h. The supernatant was then collected and the concentration of IL23p19 was determined by ELISA, and the specific procedures were carried out according to Ebioscience's instructions. After 48 hours of transfection, BMDC was stimulated with LPS for 6 h and harvested, and nucleus proteins were extracted. The protein concentration was measured by the BCA method. The amount of c-Rel protein in the nucleus was measured by Western blotting.

Figure 3:
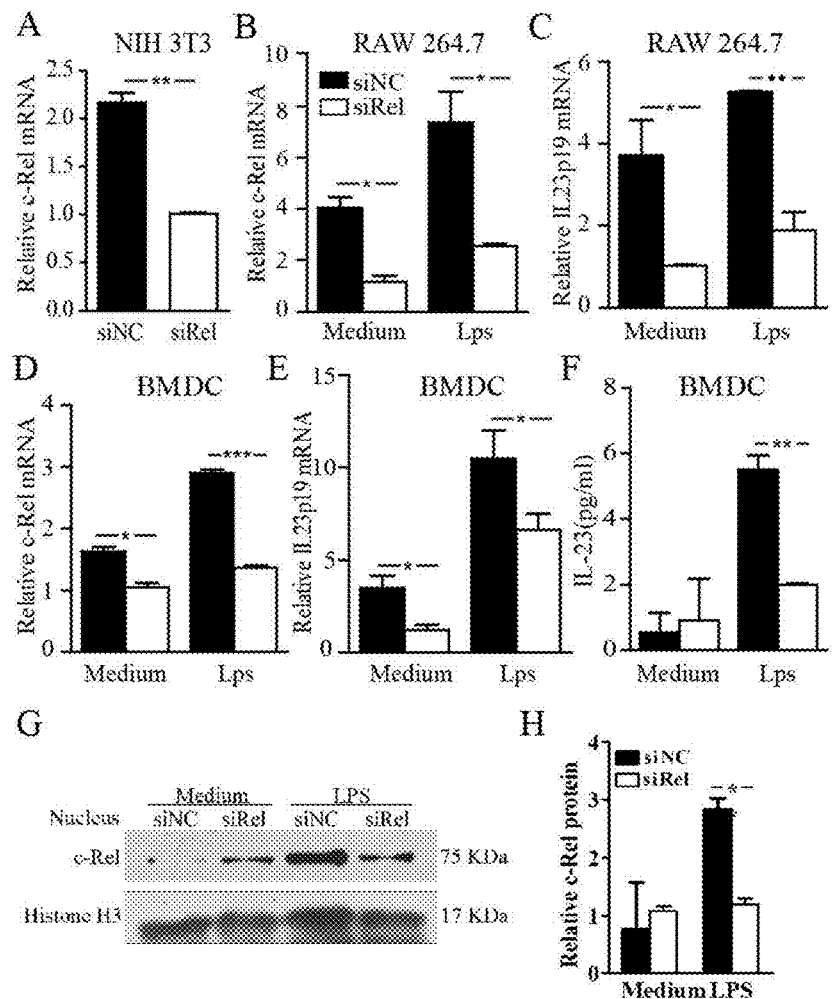
FIG. 3 illustrates in vitro silencing effect of the siRel/PEG-PLL-PLLeu nano-micelle, in which panel A-E show the relative expression of c-Rel or IL23p19 assayed by real-time quantitative PCR, in NIH3T3, RAW264.7 and BMDC stimulated with LPS for 4 hours or not stimulated after 24 hours of siNC or siRel treatment; panel F shows the protein level of IL23 in supernatant assayed by ELISA, in BMDC stimulated with LPS for 4 hours or not stimulated after 48 hours of siNC or siRel treatment; and panel G-H show that the siRel can reduce the expression of c-Rel at protein level, wherein panel H shows a chart of the quantitation of western blotting. The values are shown as mean±standard deviation (n=3), *: $P<0.05$; : $P<0.01$; *: $P<0.001$.

FIG. 3 shows the in vitro silencing effect when siRel is delivered using PEG-PLL-PLLeu nano-micelles. In panels A-C, it is demonstrated that the siRel can effectively reduce the level of c-Rel mRNA in NIH 3T3 ($P<0.01$) and the siRel can significantly decrease the mRNA level of c-Rel and IL23p19 in the RAW 264.7 cell line ($P<0.05$). When the PEG-PLL-PLLeu micelles are used to transport siRNA to BMDC and the silencing effect of the siRel is evaluated, panels D-E demonstrate that the siRel can significantly reduce the mRNA expression of c-Rel and IL23p19 in BMDC at mRNA level ($P<0.05$). Panel F shows that the siRel can also reduce the expression of IL23 at protein level ($P<0.01$). Panels G-H demonstrate that the siRel can reduce the expression of c-Rel at protein level, where panel H is a quantitative chart of the western blotting.

Example 2

Psoriasis treatment can be categorized into early stage, mid-stage and late stage treatments, in accordance with mild, moderate, and severe psoriasis in terms of severity thereof, respectively. In this experiment, the therapeutic effect of siRel was evaluated in mice with mild and moderate psoriasis. The IMQ-induced psoriasis model is similar to human psoriasis in terms of the pathological changes, and is an ideal model for studying psoriasis. IMQ is a toll-like receptor (TLR) 7/8 agonist, and when applied to the skin of mice, can activate dendritic cells and macrophages through the TLR pathway and activate keratinocytes through the TLR-independent pathways, promote the secretion of IFN-$\alpha$, TNF-$\alpha$, and other proinflammatory factors, and recruit inflammatory cells into the skin, resulting in psoriasis-like lesions and histological changes. In addition, Leslie van der Fits et al. have confirmed that the IL-23/IL-17A inflammatory axis played a critical role in the IMQ-induced psoriasis model. In contrast to the reports in the art, in the experiment in this Example in the present invention, the given IMQ dosage was increasing, because different IMQ drug manufacturers and different feeding environments for mice require different dosages for psoriasis induction.

1. Construction of IMQ-Induced Psoriasis Model

BALB/c mice were anesthetized by intraperitoneal injection of 10% chloral hydrate (300 mg/kg), followed by removing of the hair on the back to form an exposed area of about 2 cm×3 cm. IMQ was applied daily (days 0-3: 65 mg/day; day 4-day 5: 80 mg/day; day 6-day 7: 100 mg/day), and the skin of the mice was observed daily and scored for the formation of scales. The criteria of scoring is as follows: 0, no; 1, mild; 2, moderate; 3, severe; 4, critical. Scores of mice from each group were averaged and then plotted as a trend line, and the changes to the skin lesions in each group were observed.

2. siRel Treatment of Mice with Mild Psoriasis

During the construction of the psoriasis model in mice, mice having a psoriasis score of 0.5 were treated by administration of siRNA drugs. The mice with psoriasis were randomly divided into a control group (siNC) and a treatment group (siRel), and were treated on days 1, 2, 4, 6, respectively with the siNC/PEG-PLL-PLLeu and siRel/PEG-PLL-PLLeu micelle suspensions, wherein the siRNA dose was 500 pmol and the micelle dose was 100 μg. Mouse skin was observed daily and scored for the formation of scales. Mouse skin was taken on day 8 when the lesion tissues were clipped from mice in each group at the same location following a nine-grid approach, and fixed in 4% paraformaldehyde. After OCT embedding, slices having a thickness of 7 μm were obtained by cryotomy. H & E staining was then performed, and the changes to the skin thickness from mice in each group were observed.

3. siRel Treatment of Mice with Moderate Psoriasis

During the construction of the psoriasis model in mice, mice having a score of 2 were treated by administration of siRNA drugs. The mice with psoriasis were randomly divided into a control group (siNC) and a treatment group (siRel), and were treated on days 3, 4, 5, 6, 7, respectively with the siNC/PEG-PLL-PLLeu and siRel/PEG-PLL-PLLeu micelle suspensions, wherein the siRNA dose was 500 pmol and the micelle dose was 100 μg. Mouse skin was observed daily and scored for the formation of scales. Mouse skin was taken on day 8 when the lesion tissues were clipped from mice in each group at the same location following a nine-grid approach, and fixed in 4% paraformaldehyde. After OCT embedding, slices having a thickness of 7 μm were obtained by cryotomy. H & E staining was then performed, and the changes to the skin thickness from mice in each group.

Figure 4:
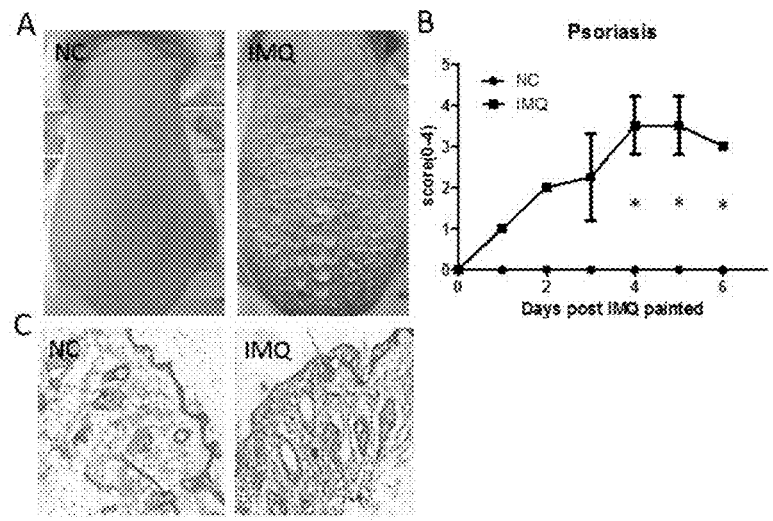
FIG. 4 illustrates the establishment of an IMQ-induced psoriasis model in mice, in which panel A shows the psoriasis phenotype at day 6 of IMQ induction of psoriasis in BALB/c mice (days 0-3: 65 mg/day; days 4-5: 80 mg/day; day 6: 100 mg/day); panel B shows scoring (0-4) of the mice skin lesions each day during the IMQ induction; and panel C shows the H & E staining of skin in the skin lesion areas of the mice of the control group and the IMQ-induced group on day 6. The values are shown as mean±standard deviation (n=3), unpaired t-test, *: $P<0.05$.

FIG. 4 shows the construction of a psoriasis model in mice using IMQ. In this figure, panel A demonstrates the psoriasis phenotype of mice in the control group and the IMQ-induced group on day 7, where apparent scales can be observed on the back of the mice in the IMQ-induced group. Panel B shows the scoring of the scale-like symptoms in the process of the psoriasis induction using IMQ, in which it can be found that scale scores of the mice in the induction group keep increasing while the control group shows almost no scale symptom, significant ($P<0.05$) on day 4, 5, 6. Panel C shows the H & E staining results of the skin sections from the mice in the control group and the IMQ-induced group on day 6, in which it can be found that the skin thickness of the mice in the IMQ-induced group is substantially thickened as compared to that of the control group. These data suggest that the IMQ dosage used in this experiment may successfully induce the psoriasis model in mice.

Figure 5:
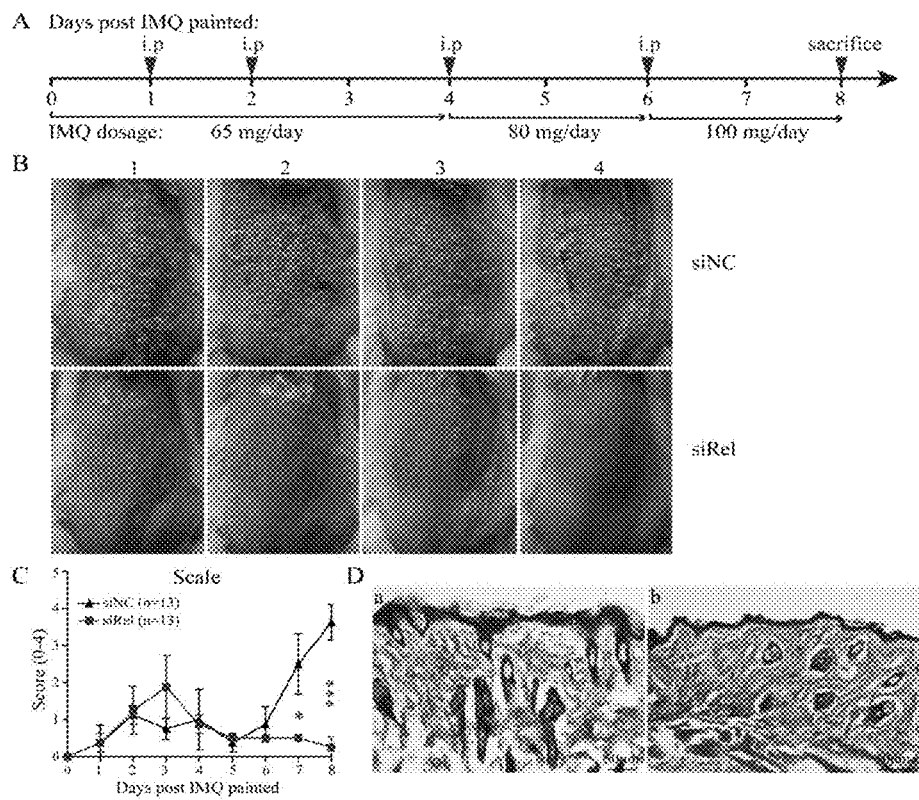
FIG. 5 illustrates siRel treatment can effectively control the development of mild psoriasis, in which panel A shows a chart of the treatment course for BALB/c mice with psoriasis where 8-11 weeks old mice were daily applied with imiquimod cream on the back for 8 consecutive days (days 0-3: 65 mg/day; days 4-5: 80 mg/day; days 6-7: 100 mg/day), intraperitoneally given siNC or siRel on days 1, 2, 4, and 6, and then sacrificed and sampled on day 8; panel B shows the phenotypes of the mice in the control group and the treatment group on day 8; panel C shows scoring (0-4) of skin lesions in mice from each group each day during the course of the treatment; and panel D shows the H & E staining of skin in the skin lesion areas of the mice from the control group and the treatment group. The values are shown as mean±standard deviation(n=13), unpaired t-test, *: $P<0.05$; ***: $P<0.001$.

FIG. 5 shows the efficacy of in vivo treatment of mild psoriasis by delivering siRel with PEG-PLL-PLLeu nano-micelles. In this figure, panel A shows the course of the treatment for BALB/c mice psoriasis. Panel B shows the psoriasis symptoms of the mice on day 8, in which it may be seen that the psoriasis-like lesions in the treatment group are substantially controlled. Panel C shows the scoring of mouse psoriasis-like symptoms, in which it may be found that the psoriasis score of the mice in the treatment group remains at a relatively low level while the psoriasis score of the mice in the control group is increasing, significant (P<0.05) on day 7 and 8. Panel D shows the H & E staining results of the skin sections from the mice in the treatment group and the control group, in which it may be found that the skin of the treated group is thinner than that of the control group, and the inflammatory cells infiltrated into the skin of the mice in the treated group are significantly reduced. These data suggest that siRel is able to effectively control the development of mild autoimmune psoriasis in mice.

Figure 6:
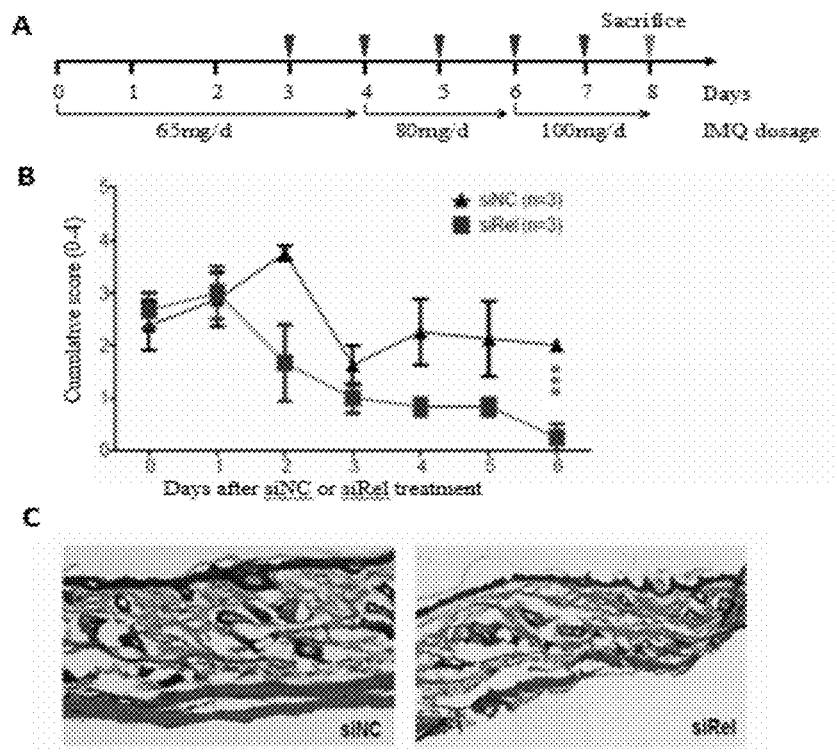
FIG. 6 illustrates siRel treatment can effectively improve the symptom of skin lesions in moderate psoriasis, in which panel A shows a chart of the treatment course for psoriasis; and panel B shows the H & E staining of skin in the skin lesion areas of the mice from the control group (siNC) and the treatment group (siRel).

FIG. 6 shows the efficacy of in vivo treatment of moderate psoriasis by delivering siRel with PEG-PLL-PLLeu nanomicelles. In this figure, panel A shows the course of the treatment for BALB/c mice psoriasis. Panel B shows the scoring of mouse psoriasis-like symptoms, in which it may be found that the psoriasis score of the mice in the treatment group keeps decreasing while the psoriasis score of the mice in the control group remains around score 2, significant (P<0.001) on day 8. Panel C shows the H & E staining results of the skin sections from the mice in the treatment group and the control group, in which it may be found that the skin of the treated group was thinner than that of the control group. These results suggest that siBel is able to effectively improve the symptoms of moderate autoimmune psoriasis in mice.

4. ELISA Assaying of the Level of IL-17A Production in Mouse Spleen Cells

During the treatment of mice with mild psoriasis, the mice were sacrificed by cervical dislocation on day 2, 6, and 8, and the spleens of the psoriasis mice in the treatment group and the control group were taken and pulverized into cell suspensions. $2\times10^6$ cells in a 500 µl culture system were inoculated in a 48-well plate. 48 h after stimulation with or without 0.5 µg/ml anti-CD3 antibodies and anti-CD28 antibodies, the supernatant was collected and assayed by enzyme-linked immunosorbent assay (ELISA) for the IL-17A level. The ELISA kit was purchased from Ebioscience, and the specific procedures were followed according to the instructions.

Figure 7:
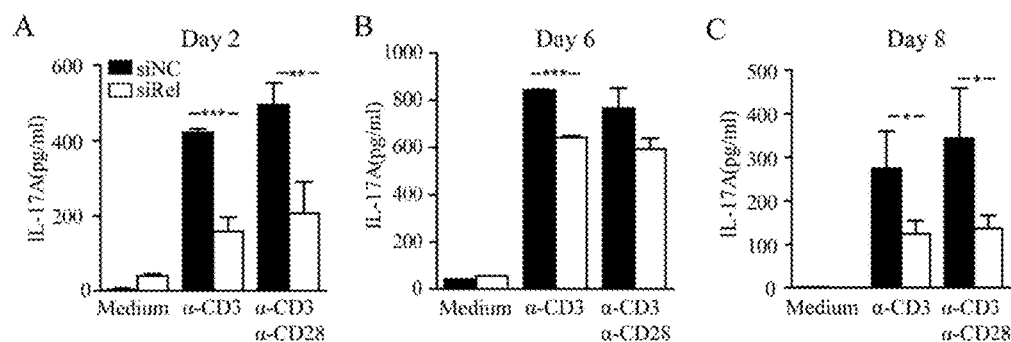
FIG. 7 illustrates the protein level of IL17A assayed by ELISA in the spleen cells of mice in the siRel treatment group. The values in this figure are shown as mean±standard deviation(n=5), unpaired t-test, *: $P<0.05$; : $P<0.01$; *: $P<0.001$.

FIG. 7 shows the level of IL-17A production in the mouse spleen cells detected by ELISA on day 2, 6, and 8 during the treatment of mice with mild psoriasis. The results suggest that on day 2, 6, and 8, the secretion of IL17A in the spleen cells of the treated group is significantly lower than that in the control group (P<0.05), indicating that siRel can effectively reduce the level of IL-17A production in spleen cells of mice with psoriasis.

5. Q-PCR Detection of Expression of IL-23/IL-17A Inflammatory Axis-Related Inflammatory Factors in Mouse Skin In the treatment of mice with mild psoriasis, lesion tissues were clipped on day 2 and 6 from the mice in each group at the same location following a nine-grid approach, placed into liquid nitrogen, and then pulverized into powder, into which the Trizol reagent to extract total RNA from the skin. Using oligo dT as a primer, reverse transcription was performed with the M-MLV Reverse Transcriptase, following the experimental operations according to the instructions of the Promega product. Then, a real-time quantitative PCR was performed by using Thunderbird SYBR qPCR Mix, with GAPDH as an internal reference, to measure the relative expression of inflammatory factors such as IL-23p19, IL-17A, IL-1β, IL-6, and TNF-α.

Figure 8:
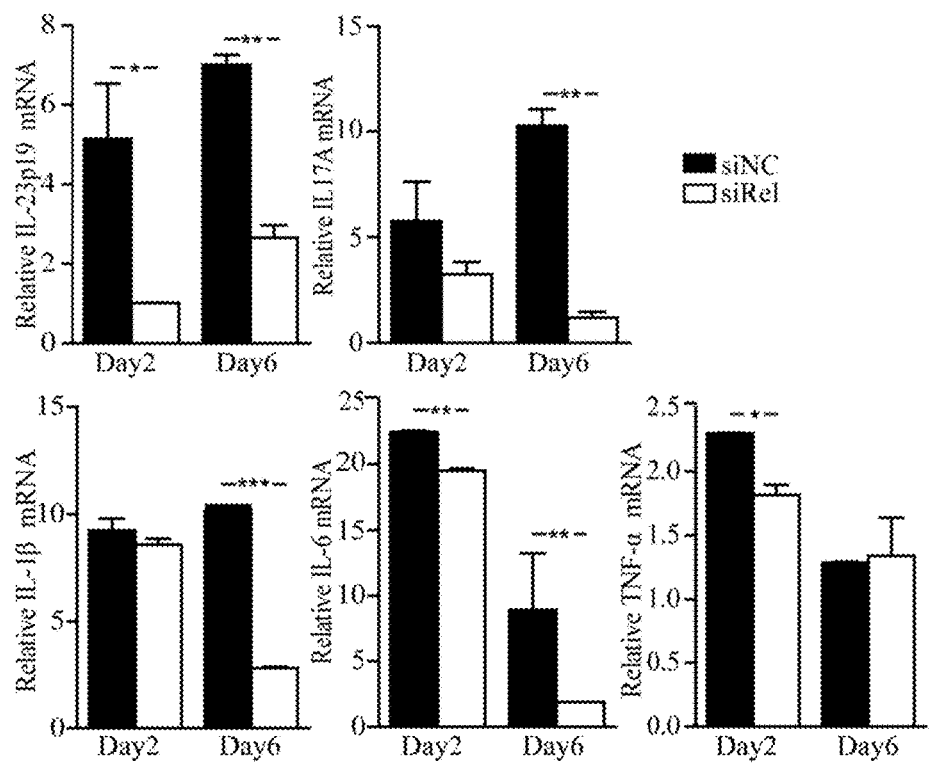
FIG. 8 illustrates the expressions of IL-23p19, IL-17A, IL-1β, IL-6 and TNF-α assayed by real-time quantitative PCR after the siRel treatment. The values are shown as mean±standard deviation(n=5), unpaired t-test, *: P<0.05; : P<0.01; *: P<0.001.
Figure 9:
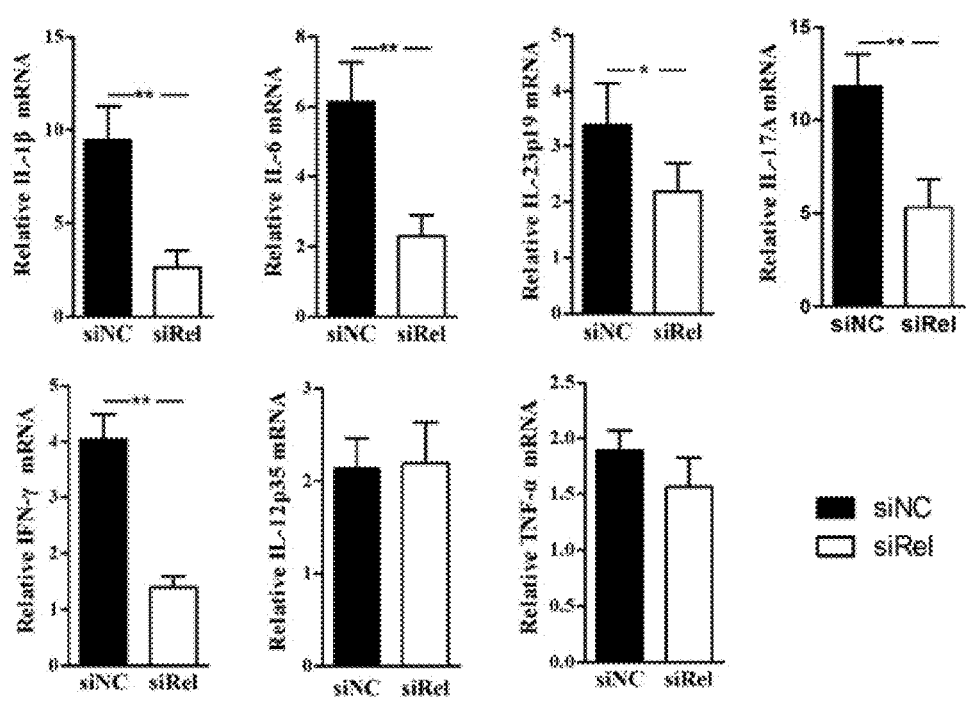
FIG. 9 illustrates the expression of inflammatory factors in the skin of mice detected by Q-PCR on day 6 after treating the mice with moderate psoriasis.

FIG. 8 shows the expression level of inflammatory factors detected by Q-PCR in mouse skin on day 2 and 6 during the treatment of mice with mild psoriasis. The results suggest that the levels of TNF-α in the skin from the mice in the treatment group and the control group decrease slightly (P<0.05), with no difference detected on day 8. In addition, the levels of IL23p19 and IL6 in the skin from the mice in the treated group significantly decrease on day 2 and day 6 (P<0.05). Moreover, as detected in the present invention, the expression levels of IL17A and IL-1β in the skin from the mice in the treated group and the control group show no difference on day 2 but a significant decrease in the treated group (P<0.01) on day 6. The above results indicate that the inflammatory response in the skin from the mice with mild psoriasis in the treated group is controlled to certain extent. FIG. 9 shows the Q-PCR detected expression level of inflammatory factors in the skin of mice with moderate psoriasis on day 6 after the treatment. The results suggest that the expression levels of IL-1β, IL-6, IL-23p19, IL-17A, and IFN-γ in the skin from the mice with moderate psoriasis in the treated group are significantly reduced as compared to those in the control group on day 6 after the treatment (P<0.05). However, there was no significant difference in the expression levels of IL-12p35 and TNF-α. The above results suggest that the inflammatory response in the skin from the mice with moderate psoriasis in the treated group is substantially improved.

Although specific embodiments of the invention have been described above, the scope of the invention should not be limited thereto. Any changes and substitutions that can be contemplated by persons skilled in the art without creative efforts in view of the technical scope disclosed in the invention are intended to be encompassed in the protection scope of the present invention.

The invention claimed is:

1. A method for preventing and/or treating autoimmune psoriasis of human, comprising a step of administrating to a subject in need thereof an effective amount of c-Rel-specific small interfering RNAs to inhibit c-Rel biosynthesis, so as to inhibit IL-23/IL-17A inflammatory axis in the subject with psoriasis
   wherein a delivery method of the small interfering RNA is selected from a group consisting of intravenous administration, intradermal application within skin lesion areas, subcutaneous application within the skin lesion areas, and on-skin application within the skin lesion areas,
   wherein a dosage of the c-Rel-specific small interfering RNAs administrated intravenously is 0.3 mg/kg, given at a frequency of once every three weeks;
   a dosage of the c-Rel-specific small interfering RNAs administrated intradermally is 8 mg in a volume of 2 ml, given at a frequency of once every one week;
   a dosage of the c-Rel-specific small interfering RNAs administrated subcutaneously is 16 mg in a volume of 4 ml, given at a frequency of once every one week; and
   a concentration of the c-Rel-specific small interfering RNAs applied on the skin is 10 nM, given at a frequency of 1-3 times every one day.

2. The method according to claim 1, wherein the c-Rel-specific small interfering RNAs have sequences as shown in SEQ ID Nos. 1-2 or SEQ ID Nos. 3-4.

3. The method according to claim 1, wherein a nano-material is used to carry the c-Rel-specific small interfering RNAs and transport them to a cytoplasm.

4. The method according to claim 3, wherein the nano-material is a PEG-PLL-PLLeu tri-block copolymer nano-micelle.

5. The method according to claim 4, wherein the dosage of the c-Rel-specific small interfering RNAs administrated intravenously is 0.3 mg/kg, and a corresponding dosage of the nano-micelle is 4.5 mg/kg, given at a frequency of once every three weeks; the dosage of the c-Rel-specific small interfering RNAs administrated intradermally is 8 mg, and a corresponding dosage of the nano-micelle is 8 mg, given at a volume of 2 ml and a frequency of once every one week; the dosage of the c-Rel-specific small interfering RNAs administrated subcutaneously is 16 mg, and a corresponding dosage of the nano-micelle is 16 mg, given at a volume of 4 ml and a frequency of once every one week; and a concentration of the c-Rel-specific small interfering RNAs applied on the skin is 10 nM, and a corresponding dosage of the nano-micelle is 10 µg/ml, given at a frequency of 1-3 times every one day, wherein 0.5 ml of a c-Rel-specific small interfering RNAs-nano-micelle suspension is applied per 500 square centimeters for each application.

6. A method for preventing and/or treating autoimmune psoriasis, comprising a step of administrating to a subject in need thereof an effective amount of c-Rel-specific small interfering RNAs to inhibit c-Rel biosynthesis, so as to inhibit IL-23/IL-17A inflammatory axis in the subject,
   wherein the subject is a mammal,
   wherein for in vitro administration, the c-Rel-specific small interfering RNAs used at a concentration of 10-100 nM; for in vivo administration, for treatment of mild psoriasis, each mammal is administered intraperitoneally 500 pmol c-Rel-specific small interfering RNAs, given at a frequency of once every two days; for treatment of moderate psoriasis, each mammal is administered intraperitoneally 500 pmol c-Rel-specific small interfering RNAs, given at a frequency of once every one day.

7. The method according to claim 6, wherein the c-Rel-specific small interfering RNAs have sequences as shown in SEQ ID Nos. 1-2 or SEQ ID Nos. 3-4.

8. The method according to claim 6, wherein a nano-material is used to carry the c-Rel-specific small interfering RNAs and transport them to the cytoplasm.

9. The method according to claim 6, wherein the nano-material is a PEG-PLL-PLLeu tri-block copolymer nano-micelle.

10. The method according to claim 9, wherein the subject is a mouse.

11. The method according to claim 10, wherein, for in vitro administration, the c-Rel-specific small interfering RNAs is used at a concentration of 10-100 nM, and the nano-micelle is used at a concentration of 10-20 μg/ml; for in vivo administration, for the treatment of mild psoriasis, each mouse is administered intraperitoneally 500 pmol of the c-Rel-specific small interfering RNAs, corresponding to 100 μg of nano-micelle, given at a frequency of once every two days; for the treatment of moderate psoriasis, each mouse is administered intraperitoneally 500 pmol of the c-Rel-specific small interfering RNAs, corresponding to 100 μg of nano-micelle, given at a frequency of once every one day.

\* \* \* \* \*

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: c-Rel-specific siRNA

<400> SEQUENCE: 1
caaccggaca uacccgucu                                                19

<210> SEQ ID NO 2
<211> LENGTH: 19

```
<212> TYPE: DNA
<213> ORGANISM: Artificial Sequence
<220> FEATURE:
<223> OTHER INFORMATION: c-Rel-specific siRNA

<400> SEQUENCE: 2
agacggguau guccgguug                                                    19

<210> SEQ ID NO 3
<211> LENGTH: 19
<212> TYPE: DNA
<213> ORGANISM: Artificial Sequence
<220> FEATURE:
<223> OTHER INFORMATION: c-Rel-specific siRNA

<400> SEQUENCE: 3
caaccgaaca uacccuucu                                                    19

<210> SEQ ID NO 4
<211> LENGTH: 19
<212> TYPE: DNA
<213> ORGANISM: Artificial Sequence
<220> FEATURE:
<223> OTHER INFORMATION: c-Rel-specific siRNA

<400> SEQUENCE: 4
agaaggguau guucgguug                                                    19
```